(12) United States Patent
Fiorella (10) Patent No.: US 8,591,548 B2
(45) Date of Patent: Nov. 26, 2013

(54) SPINOUS PROCESS FUSION PLATE ASSEMBLY

(75) Inventor: David L. Fiorella, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 147 days.

(21) Appl. No.: 13/077,398

(22) Filed: Mar. 31, 2011

(65) Prior Publication Data

US 2012/0253393 A1    Oct. 4, 2012

(51) Int. Cl.
A61B 17/70    (2006.01)

(52) U.S. Cl.
USPC ........................................................ 606/249

(58) Field of Classification Search
USPC .................... 606/246–249; 623/17.11–17.16
See application file for complete search history.

(56) References Cited

U.S. PATENT DOCUMENTS

| | | |
|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |

(Continued)

FOREIGN PATENT DOCUMENTS

| | | |
|---|---|---|
| DE | 2821678 A1 | 11/1979 |
| DE | 3922044 A1 | 2/1991 |

(Continued)

OTHER PUBLICATIONS

"Dispositivo Intervertebrale Ammortizzante DIAM," date unknown, p. 1.

(Continued)

Primary Examiner — Jan Christopher Merene
Assistant Examiner — Steven Cotroneo (57) ABSTRACT

A spinal implant helps stabilize vertebrae for fusion. The implant includes first and second plates, a brace and a locking mechanism. When installed, the plates extend superiorly-inferiorly along respective lateral sides of the spinous processes. The plates are moved toward one another and relative to the brace by the locking mechanism to clamp the implant to the spinous processes.

18 Claims, 6 Drawing Sheets

(56) References Cited

U.S. PATENT DOCUMENTS

| | | |
|---|---|---|
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,245,107 B1 | 6/2001 | Ferree |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 * | 5/2006 | Robinson et al. ............ 606/86 B |

(56) References Cited

U.S. PATENT DOCUMENTS

| | | |
|---|---|---|
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,763,073 B2 * | 7/2010 | Hawkins et al. ............ 623/17.11 |
| 7,771,456 B2 | 8/2010 | Hartman et al. |
| 7,862,615 B2 | 1/2011 | Carli et al. |
| 7,901,430 B2 | 3/2011 | Matsuura et al. |
| 8,128,702 B2 * | 3/2012 | Zucherman et al. ....... 623/17.16 |
| 2001/0016743 A1 | 8/2001 | Zucherman et al. |
| 2002/0143331 A1 | 10/2002 | Zucherman et al. |
| 2003/0040746 A1 * | 2/2003 | Mitchell et al. ................. 606/61 |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0010312 A1 | 1/2004 | Enayati |
| 2004/0010316 A1 | 1/2004 | William et al. |
| 2004/0087947 A1 | 5/2004 | Lim et al. |
| 2004/0097931 A1 | 5/2004 | Mitchell |
| 2004/0106995 A1 | 6/2004 | LeCouedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049708 A1 | 3/2005 | Atkinson et al. |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 * | 11/2006 | Blackwell et al. ............... 606/71 |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyer et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 * | 3/2008 | Malandain et al. ........ 623/17.11 |
| 2008/0097446 A1 | 4/2008 | Reiley et al. |

(56) References Cited

U.S. PATENT DOCUMENTS

| | | | |
|---|---|---|---|
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0183209 A1 | 7/2008 | Robinson et al. | |
| 2008/0183211 A1 | 7/2008 | Lamborne et al. | |
| 2008/0183218 A1* | 7/2008 | Mueller et al. | 606/280 |
| 2008/0195152 A1 | 8/2008 | Altarac et al. | |
| 2008/0215094 A1 | 9/2008 | Taylor | |
| 2008/0221685 A9 | 9/2008 | Altarac et al. | |
| 2008/0234824 A1 | 9/2008 | Youssef et al. | |
| 2008/0262617 A1* | 10/2008 | Froehlich et al. | 623/14.12 |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0105766 A1 | 4/2009 | Thompson et al. | |
| 2009/0105773 A1 | 4/2009 | Lange et al. | |
| 2009/0234389 A1 | 9/2009 | Chuang et al. | |
| 2009/0240283 A1 | 9/2009 | Carls et al. | |
| 2009/0270918 A1 | 10/2009 | Attia et al. | |
| 2010/0087869 A1* | 4/2010 | Abdou | 606/279 |
| 2010/0121379 A1 | 5/2010 | Edmond | |
| 2010/0204732 A1 | 8/2010 | Aschmann et al. | |
| 2010/0211101 A1 | 8/2010 | Blackwell et al. | |
| 2012/0109198 A1* | 5/2012 | Dryer et al. | 606/248 |

FOREIGN PATENT DOCUMENTS

| | | |
|---|---|---|
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

"Tecnica Operatoria Per Il Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine Afer Dynamic Stabilization," J. Spinal Discord Tech., 2006, vol. 00, No. 00, pp. 1-7.

Benzel et al., "Posterior Cervical Interspinous Compression Wiring and Fusion for Mid to Low Cervical Spinal Injuries," J. Neurosurg., Jun. 1989, pp. 893-899, vol. 70.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

(56) References Cited

OTHER PUBLICATIONS

Hambly et al., "Tension Band Wiring-Bone Grafting for Spondylolysis and Spondylolisthesis," Spine, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Kramer et al., "Intervetertebral Disk Diseases: Causes, Diagnosis, Treatment and Prophylaxis," pp. 244-249, Medical, 1990.
Laudet et al., "Comportement Bio-Mécanique D'Un Ressort Inter-Apophysaire Verteébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," Spine, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Implanto Posteriore Ammortizzante," S.O.T.I.M.I. Societàdi Ortopedia e Traumatologia dell'Italia Meridionale e Insulare 90° Congresso, Jun. 21-23, 2001, Paestum.
Petrini et al., "Stabilizzazione Elastica," Patologia Degenerativa del Rachide Lombare, Oct. 5-6, 2001, Rimini.
Phillips et al., "Biomechanics of Posterior Dynamic Stabiling Device (DIAM) After Facetectomy and Disectomy," The Spine Journal, 2006, vol. 6, pp. 714-722.
Porter, "Spinal Stenosis and Neurogenic Claudication," Spine, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," Spine, 2005, pp. 744-749, vol. 30, No. 7.
Scarfò, "Instability/Stenosis: Holistic Approach for Less Invasive Surgery," date unknown, University of Siena, Siena, Italy.
Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.
Schlegel et al., "The Role of Distraction in Improving the Space Available in the Lumbar Stenotic Canal and Foramen," Spine, 1994, pp. 2041-2047, vol. 19, No. 18.
Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.
Senegas et al., "Stabilisation Lombaire Souple," Instabilité Vertébrales Lombaires, Gastambide, ed., 1995, pp. 122-132, Expansion Scientifique Française, Paris, France.
Senegas, "La Ligamentoplastie Inter Vertébrale Lombaire, Alternative a L'Arthodèse," La Revue de Médecine Orthopédique, Jun. 1990, pp. 33-35, No. 20.
Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.
Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.
Senegas, "Rencontre," Maîtrise Orthopédique, May 1995, pp. 1-3, No. 44.
Serhan, "Spinal Implants: Past, Present, and Future," 19th International IEEE/EMBS Conference, Oct. 30-Nov. 2, 1997, pp. 2636-2639, Chicago, Illinois.
Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.
Sulzer Innotec, "DIAM—Modified CAD Geometry and Meshing," date unknown.
Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.
Taylor et al., "Device for Intervertebral Assisted Motion: Technique and Intial Results," 22 Neurosurg. Focus, Jan. 2007, vol. 22, No. 1, pp. 1-6.
Taylor et al., "Surgical Requirement for the Posterior Control of the Rotational Centers," date unknown.
Taylor et al., "Technical and Anatomical Considerations for the Placement of a Posterior Interspinous Stabilizer," 2004, pp. 1-10, Medtronic Sofamor Danek USA, Inc., Memphis, Tennessee.
Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.
Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.
Taylor, "Posterior Dynamic Stabilization using the DIAM (Device for Intervertebral Assisted Motion)," date unknown, pp. 1-5.
Taylor, "Présentation à un an d'un dispositif amortissant d'assistance discale," 5èmes journées Avances & Controverses en pathologie rachidienne, Oct. 1-2, 1998, Faculté Libre de Médecine de Lille.
Tsuji et al., "Ceramic Interspinous Block (CISB) Assisted Anterior Interbody Fusion," J. Spinal Disorders, 1990, pp. 77-86, vol. 3, No. 1.
Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.
Voydeville et al., "Experimental Lumbar Instability and Artificial Ligament," Eur. J. Orthop. Surg. Traumatol., Jul. 15, 2000, pp. 167-176, vol. 10.
Voydeville et al., "Lumbar Instability Treated by Intervertebral Ligamentoplasty with Smooth Wedges," Orthopédie Traumatologie, 1992, pp. 259-264, vol. 2, No. 4.
Waldemar Link, "Spinal Surgery: Instrumentation and Implants for Spinal Surgery," 1981, Link America Inc., New Jersey.
Wilke et al., "Biomedical Effect of Different Lumbar Interspinous Implants on Flexibilty and Intradiscal Pressure," Eur Spine J., Vo. 17, published online Jun. 27, 2008, pp. 1049-1056.
Wiltse et al., "The Treatment of Spinal Stenosis," Clinical Orthopaedics and Related Research, Urist, ed., Mar.-Apr. 1976, pp. 83-91, No. 115.
Wisneski et al., "Decompressive Surgery for Lumbar Spinal Stenosis," Seminars in Spine Surgery, Wiesel, ed., Jun. 1994, pp. 116-123, vol. 6, No. 2.
Zdeblick et al., "Two-Point Fixation of the Lumbar Spine Differential Stability in Rotation," Spine, 1991, pp. S298-S301, vol. 16, No. 6, Supplement.
Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.
Zucherman et al., "Clinical Efficacy of Spinal Instrumentation in Lumbar Degenerative Disc Disease," Spine, Jul. 1992, pp. 834-837, vol. 17, No. 7.

* cited by examiner

SPINOUS PROCESS FUSION PLATE ASSEMBLY

BACKGROUND

This invention relates generally to devices for the treatment of spinal conditions, and more particularly, to the treatment of various spinal conditions that cause back pain. Even more particularly, this invention relates to devices that may be placed between adjacent spinous processes to treat various spinal conditions. For example, spinal conditions that may be treated with these devices may include spinal stenosis, degenerative disc disease (DDD), disc herniations and spinal instability, among others.

The clinical syndrome of neurogenic intermittent claudication due to lumbar spinal stenosis is a frequent source of pain in the lower back and extremities, leading to impaired walking, and causing other forms of disability in the elderly. Although the incidence and prevalence of symptomatic lumbar spinal stenosis have not been established, this condition is the most frequent indication of spinal surgery in patients older than 65 years of age.

Lumbar spinal stenosis is a condition of the spine characterized by a narrowing of the lumbar spinal canal. With spinal stenosis, the spinal canal narrows and pinches the spinal cord and nerves, causing pain in the back and legs. It is estimated that approximately 5 in 10,000 people develop lumbar spinal stenosis each year. For patients who seek the aid of a physician for back pain, approximately 12%-15% are diagnosed as having lumbar spinal stenosis.

Common treatments for lumbar spinal stenosis include physical therapy (including changes in posture), medication, and occasionally surgery. Changes in posture and physical therapy may be effective in flexing the spine to decompress and enlarge the space available to the spinal cord and nerves—thus relieving pressure on pinched nerves. Medications such as NSAIDS and other anti-inflammatory medications are often used to alleviate pain, although they are not typically effective at addressing spinal compression, which is the cause of the pain.

Surgical treatments are more aggressive than medication or physical therapy, and in appropriate cases surgery may be the best way to achieve lessening of the symptoms of lumbar spinal stenosis and other spinal conditions. The principal goal of surgery to treat lumbar spinal stenosis is to decompress the central spinal canal and the neural foramina, creating more space and eliminating pressure on the spinal nerve roots. The most common surgery for treatment of lumbar spinal stenosis is direct decompression via a laminectomy and partial facetectomy. In this procedure, the patient is given a general anesthesia and an incision is made in the patient to access the spine. The lamina of one or more vertebrae may be partially or completely removed to create more space for the nerves. The success rate of decompressive laminectomy has been reported to be in excess of 65%. A significant reduction of the symptoms of lumbar spinal stenosis is also achieved in many of these cases.

The failures associated with a decompressive laminectomy may be related to postoperative iatrogenic spinal instability. To limit the effect of iatrogenic instability, fixation and fusion may also be performed in association with the decompression. In such a case, the intervertebral disc may be removed, and the adjacent vertebrae may be fused. A discectomy may also be performed to treat DDD and disc herniations. In such a case, a spinal fusion would be required to treat the resulting vertebral instability. Spinal fusion is also traditionally accepted as the standard surgical treatment for lumbar instability.

A wide variety of spinal fusion devices are used following partial or total discectomies for stabilization of the spine at that site. Many such devices are secured extradiscally, such as to the pedicles or spinous processes. For example, the spinous process fusion plate available from Medtronic, Spinal and Biologics of Memphis, Tenn. under the brand name CD Horizon Spire is typically secured to the spinous processes. See for example the devices and methods disclosed in U.S. Pat. Nos. 7,048,736 and 7,727,233, the entire contents of which are expressly incorporated herein by reference. These devices typically work for there intended purposes. However, with the demands of spinal surgery, the medical device industry is continually looking for ways to improve currently available devices.

SUMMARY

The spinal implant described herein may include first and second plates, a brace extending between the plates and a locking mechanism that moves the two plates toward each other and locks them in an appropriate relative position. When installed in the patient's anatomy, the brace extends laterally through the interspinous space, and the plates extend superiorly-inferiorly along respective lateral sides of the spinous processes.

The first plate and the second plate may each have a generally linear longitudinal axis or may extend along curved longitudinal axes or may have a longitudinal axis that is off-set along its height. Each plate may also have an inner face configured to abut adjacent spinous processes with projections extending therefrom that engage or "bite into" the spinous processes. The brace may be fixed to the first plate and extend through an opening in the second plate. Alternatively, the first plate may include an opening through which the brace extends and the brace may include an enlarged proximal end that can be located on the proximal side of the first plate to prevent that plate from moving proximally with respect to the brace. The opening in the second plate allows the brace to be placed through the opening and allows the second plate to slide along the brace and thus vary the distance between the first and second plate. The axis of the brace is transverse to the longitudinal axes of the first and second plates. The brace may be a hollow tube defining a lumen extending therethrough. The plate to which the brace is affixed may also define an opening to allow a locking element to extend through the first and second plates and through the brace.

The locking element may include an enlarged distal element connected along its proximal portion to a proximal rod. The diameter of the enlarged distal element is chosen so that its maximum diameter is greater than the diameter of the lumen of the brace. The locking element is located within the lumen of the brace so that the enlarged distal element extends distally beyond the distal end of the brace and the rod extends proximally beyond the proximal end of the brace. When the locking element is pulled proximally, the enlarged distal end deforms the distal portion of the brace so the diameter of the distal portion of the brace increases so as to be greater than the diameter of the opening in the second plate, thus preventing the second plate from being moved distally off of the brace. Continued proximal movement of the locking element moves the two plates together so that the projections of each plate engage and "bite into" the spinous processes and lock the implant to the spinous processes. The proximal portion of the rod of the locking element extending from the proximal end of the brace may then be broken or cut off from enlarged distal end or the remainder of the distal portion of the rod.

A method of implanting the spinal implant may include the following steps. After access to the desired spinal motion segment is obtained, a first plate is located adjacent to the proximal lateral sides of adjacent superior and inferior spinous processes. Where the brace is fixed to the first plate, placement of the first plate should be made so that the brace extends in the interspinous space through the sagittal plane. Where the brace is not fixed to the first plate, the brace is inserted through an opening in the first plate so the brace extends in the interspinous space through the sagittal plane and moved distally until an enlarged proximal tab abuts the proximal face of the first plate. The second plate is located over the brace so that the second plate is placed adjacent to the distal lateral sides of the adjacent superior and inferior spinous processes. The locking mechanism is then placed through the brace such that the proximal rod is first inserted through the distal opening to the lumen of the brace and moved proximally until the enlarged distal element abuts the distal opening of the brace. The surgeon may then pull the proximal rod from the proximal side of the brace to enlarge the distal portion of the brace. Continued proximal movement of the locking mechanism forces the enlarged distal element into the distal portion of the brace, enlarging this portion of the brace and forcing the distal plate to move proximally into engagement with the distal lateral faces of the adjacent superior and inferior spinous processes. Once the surgeon is satisfied with the placement of the implant, the surgeon may then break or cut off the proximal rod of the locking element.

DETAILED DESCRIPTION

As used in this specification and the appended claims, the singular forms "a," "an" and "the" include plural referents unless the context clearly dictates otherwise. Thus, for example, the term "a member" is intended to mean a single member or a combination of members, and "a material" is intended to mean one or more materials, or a combination thereof. Furthermore, the words "proximal" and "distal" refer to directions closer to and away from, respectively, an operator (e.g., surgeon, physician, nurse, technician, etc.) who would insert the medical device into the patient, with the tip-end (i.e., distal end) of the device inserted inside a patient's body first. Thus, for example, the device end first inserted inside the patient's body would be the distal end of the device, while the device end last to enter the patient's body would be the proximal end of the device.

Figure 1:
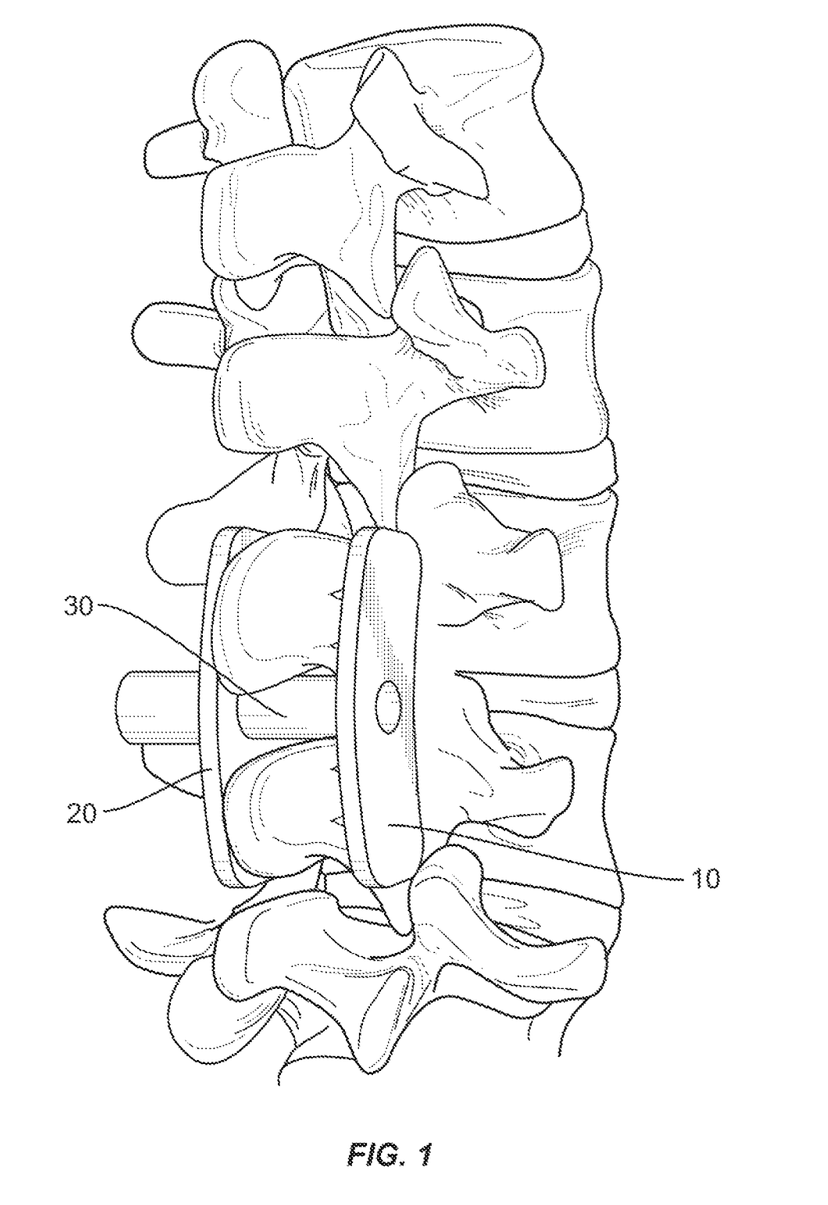
FIG. 1 is a perspective view of a spinal motion segment with a spinal implant located therein.
Figure 2:
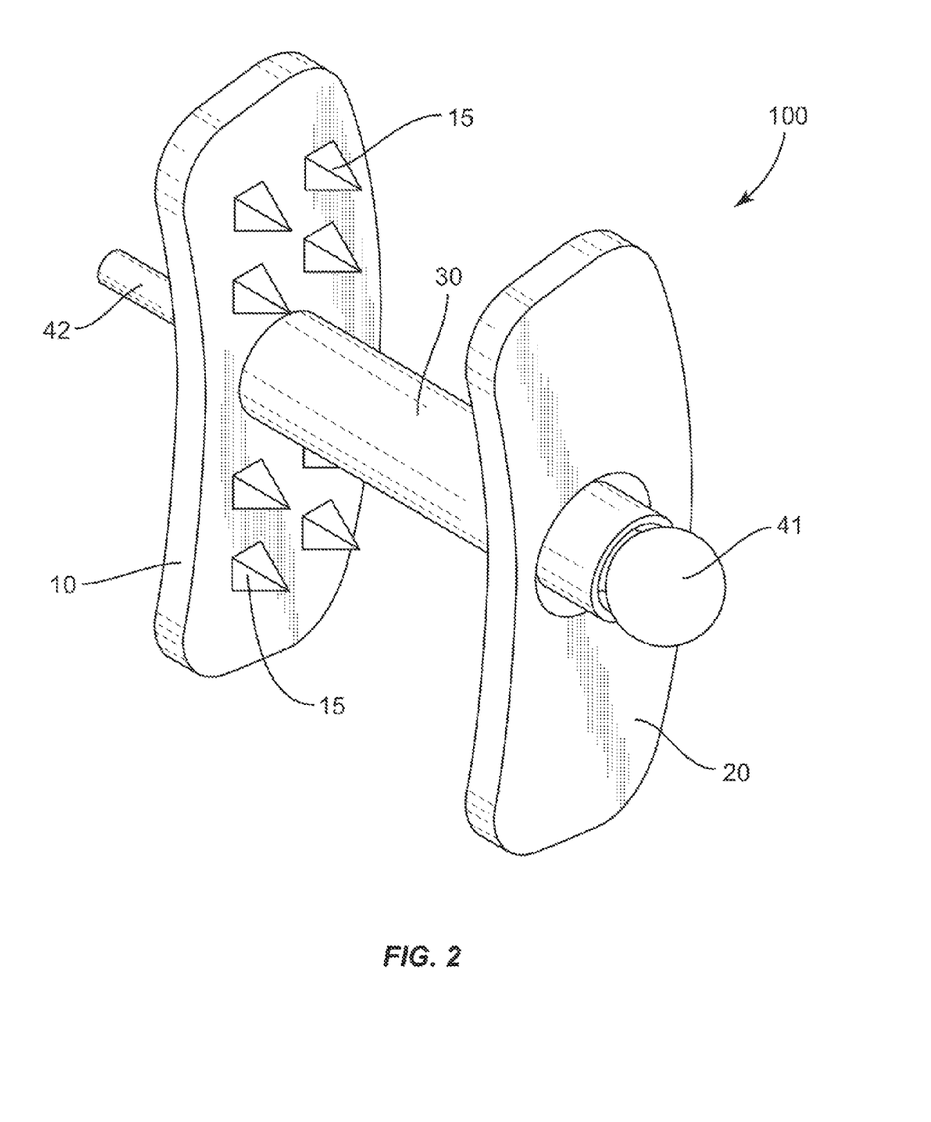
FIG. 2 is a perspective view of the opposite side of the spinal implant shown in FIG. 1.
Figure 3A:
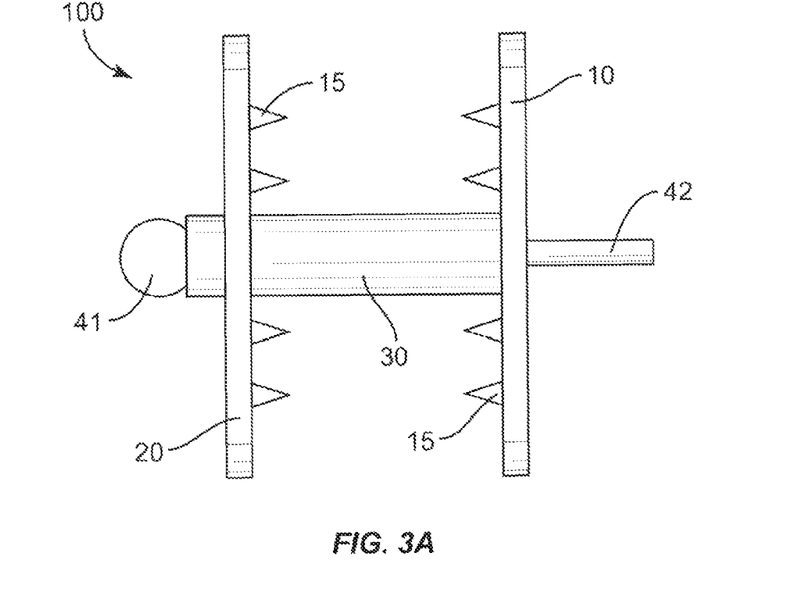
FIG. 3A is a front elevation view of a spinal implant.
Figure 3B:
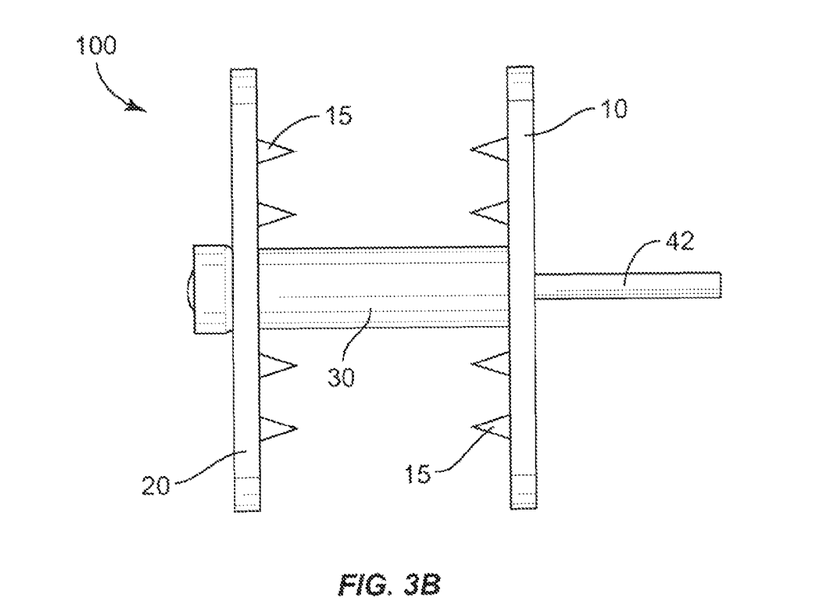
FIG. 3B is a front elevation view of the spinal implant shown in FIG. 3A but with the locking mechanism moved proximally with respect to the spinal implant.
Figure 3C:
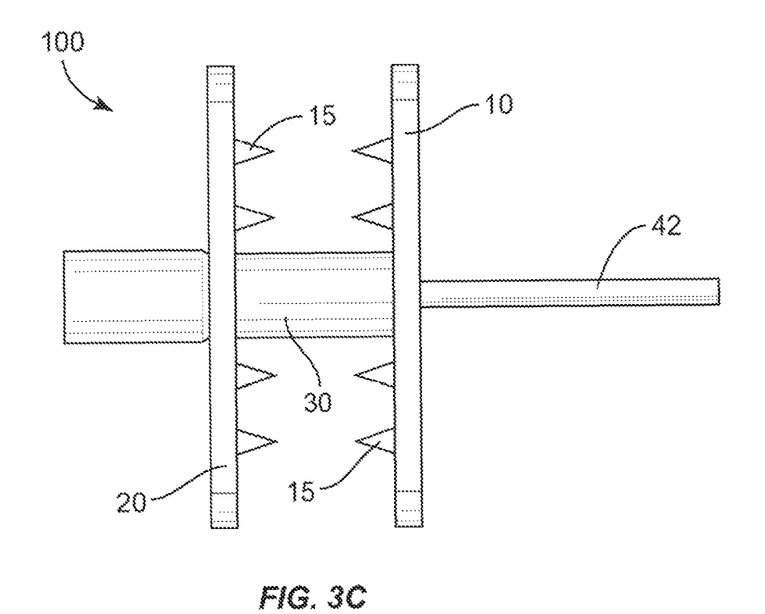
FIG. 3C is a front elevation view of the spinal implant shown in FIG. 3B but with the locking mechanism moved further proximally with respect to the spinal implant.
Figure 3D:
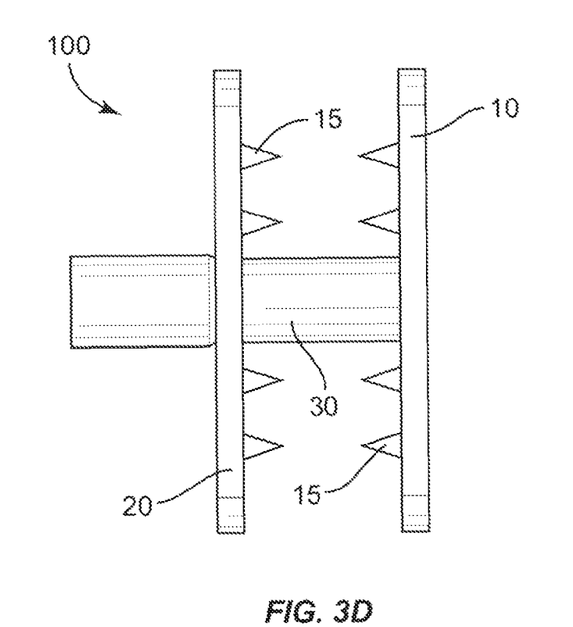
FIG. 3D is a front elevation view of the spinal implant shown in FIG. 3C but with the proximal end of the locking mechanism removed.
Figure 4:
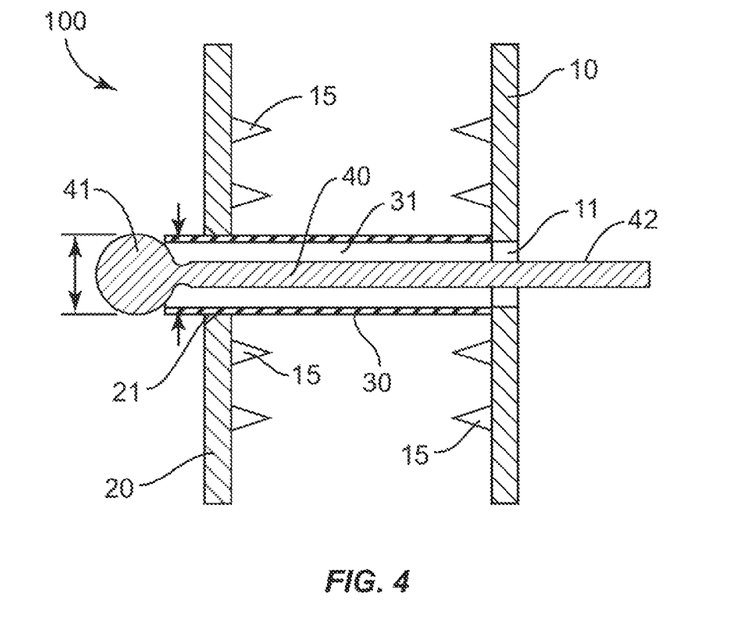
FIG. 4 is a cross-sectional view of the spinal implant shown in FIG. 3A.
Figure 5:
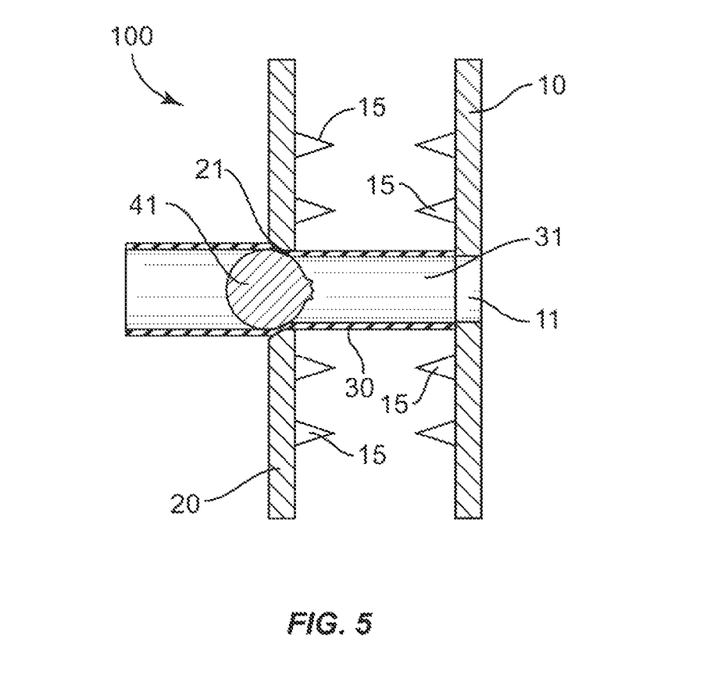
FIG. 5 is a cross-sectional view of the spinal implant shown in FIG. 3D.

As used in this specification and the appended claims, the terms "up", "upper", "top", "down", "lower", "bottom", "front", "back", "rear", "left", "right", "side", "inner", "middle" and "center", and similar terms, refer to portions of or positions in or on the implant when the implant is oriented in its implanted position, such as shown in FIG. 1.

As used in this specification and the appended claims, the term "axial plane" when used in connection with particular relationships between various parts of the implant means a plane that divides the implant into upper and lower parts. As used in this specification and the appended claims, the term "coronal plane" when used in connection with particular relationships between various parts of the implant means a plane that divides the implant into front and back parts. As used in this specification and the appended claims, the term "sagittal plane" when used in connection with particular relationships between various parts of the implant means a plane that divides the implant into left and right parts.

As used in this specification and the appended claims, the term "body" when used in connection with the location where the device of this invention is to be placed, or to teach or practice implantation methods for the device, means a mammalian body. For example, a body can be a patient's body, or a cadaver, or a portion of a patient's body or a portion of a cadaver. A "body" may also refer to a model of a mammalian body for teaching or training purposes.

As used in this specification and the appended claims, the term "parallel" describes a relationship, given normal manufacturing or measurement or similar tolerances, between two geometric constructions (e.g., two lines, two planes, a line and a plane, two curved surfaces, a line and a curved surface or the like) in which the two geometric constructions are substantially non-intersecting as they extend substantially to infinity. For example, as used herein, a line is said to be parallel to a curved surface when the line and the curved surface do not intersect as they extend to infinity. Similarly, when a planar surface (i.e., a two-dimensional surface) is said to be parallel to a line, every point along the line is spaced apart from the nearest portion of the surface by a substantially equal distance. Thus, two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

As used in this specification and the appended claims, the terms "normal", "perpendicular" and "orthogonal" describe a relationship between two geometric constructions (e.g., two lines, two planes, a line and a plane, two curved surfaces, a line and a curved surface or the like) in which the two geometric constructions intersect at an angle of approximately 90 degrees within at least one plane. For example, as used herein, a line is said to be normal, perpendicular or orthogonal to a curved surface when the line and the curved surface intersect at an angle of approximately 90 degrees within a plane. Thus two geometric constructions are described herein as being "normal", "perpendicular", "orthogonal" or "substantially normal", "substantially perpendicular", "substantially orthogonal" to each other when they are nominally 90 degrees to each other, such as for example, when they are 90 degrees to each other within a tolerance. Such tolerances can include, for example, manufacturing tolerances, measurement tolerances or the like.

A spinal implant 100 for spinal fusion that attaches to adjacent spinous processes to fixate the corresponding vertebrae relative to the other is described herein. Implant 100 may include two fixation plates 10, 20, a brace 30 and a locking element 40. Plates 10, 20 are adapted to be disposed on respective lateral sides of the adjacent superior and inferior spinous processes. Projections 15 may extend from the inner surfaces of plates 10, 20 and are adapted to engage or "bite into" the surfaces of the spinous processes to fix plates 10, 20 with respect to the spinous processes. Brace 30 may be fixed to plate 10 and is adapted to extend through at least plate 20 with distal plate 20 adapted to be moveable proximally with respect to brace 30. Brace 30 may be hollow and may define a lumen 31 extending therethrough that defines a first diameter. Locking element 40 is adapted to be disposed within lumen 31.

Figure 6:
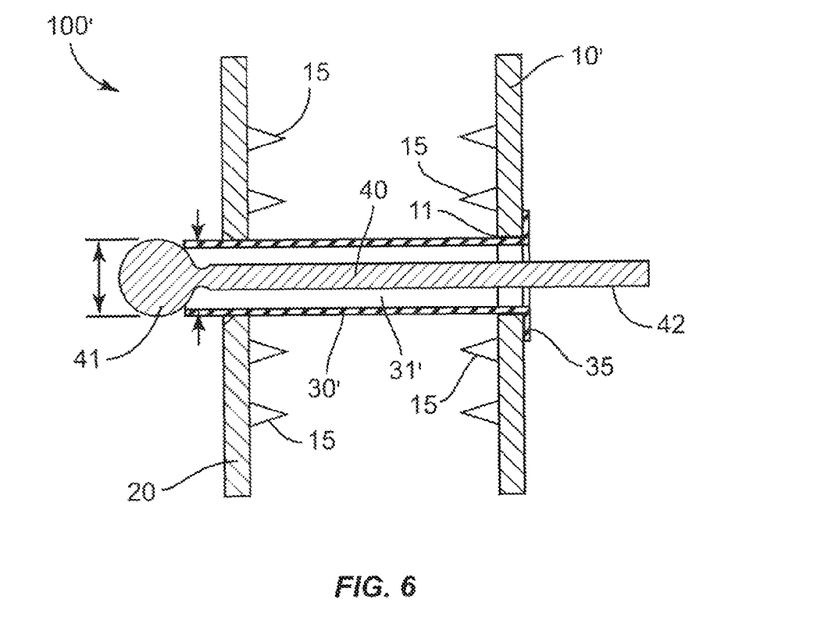
FIG. 6 is a cross-sectional view of another embodiment of a spinal implant.

Both proximal plate 10 and distal plate 20 may have a generally curved configuration that extends along a curving longitudinal axis. It is to be understood however that plates 10, 20 may be generally rectangular with a straight longitudinal axis or may have an offset configuration where the upper and lower portions of the longitudinal axis are offset from each other. Projections, or teeth, 15 extend inwardly away from the longitudinal axis of the plate on which they are located and toward the spinous process. As mentioned above, projections 15 are adapted to engage or "bite into" the surfaces of the spinous processes to fix plates 10, 20 with respect to the spinous processes. Each plate 10, 20 defines an opening 11, 21, respectively, therein along a medial portion. Opening 21 in distal plate 20 should have a diameter large enough to allow distal plate 20 to slide proximally along brace 30. Opening 11 in proximal plate 10 should have a diameter large enough to allow the proximal rod 42 of locking element 40 to slide proximally past proximal plate 10. As shown in FIG. 6, plates 10, 20 may be substantially mirror images of each other.

Brace 30 may have a generally tubular configuration defining lumen 31 therein. Brace 30 may be fixed to either plate 10, 20. As shown in FIGS. 1-5, brace 30 may be fixed along its proximal end to proximal plate 10 using any suitable means such as welding, brazing, adhesive or mechanical engagement. Distal plate 20 may define an opening 21 to allow brace 30 to extend through plate 20 and thus slide along brace 30 and vary the distance between proximal plate 10 and distal plate 20. The axis of brace 30 is generally transverse to the longitudinal axes of plates 10, 20. Proximal plate 10 may also define an opening 11 to allow proximal rod 42 to extend proximally through plate 10. As shown, in FIG. 6, brace 30' need not be fixed to plate 10'. Instead, plate 10' may define an opening 11' having a diameter to allow brace 30' to extend through plate 10'. A proximal flange 35 may be located at the proximal end of brace 30' to prevent plate 10 from moving proximally off of brace 30'. As mention above, the diameter of the proximal portion of brace 30' and the diameter of opening 11' may be matched to provide an interference fit therebetween.

Locking element 40 includes an enlarged distal knob 41 and a proximal rod 42 attached to distal knob 41. The maximum diameter of enlarged distal knob 41 is chosen so that it is greater than the diameter of lumen 31. Although knob 41 is shown in the FIGS. as having a generally circular cross-section, it is to be understood that other configurations could be used for knob 41. However, it is desirable that the proximal portion of knob 41 have a tapered proximal configuration that increases in diameter in the distal direction. This taper facilitates proximal movement of locking element 40 with respect to brace 30. Locking element 40 is disposed within lumen 31 of brace 30 so that knob 41 is initially located beyond the distal end of brace 30 and the proximal end of rod 42 extends proximally beyond the proximal end of brace 30 and plate 10. See, e.g. FIG. 4. When locking element 40 is pulled proximally, the tapered portion of knob 41 engages the distal end of brace 30 and forces the distal portion of brace 30 to deform so it increases in diameter such that the enlarged diameter is greater than the diameter of opening 21 in distal plate 20. This increase in diameter for the distal portion of brace 30 prevents plate 20 from being moved distally off of brace 30 and thus locks plate 20 to brace 30 and plate 10. In addition, since the increased diameter of the distal portion of brace 30 caused by knob 41 is larger than the diameter of opening 21, proximal movement of knob 41 forces plate 20 to move proximally. Continued proximal movement of locking element 40 moves plates 10, 20 together so that projections 15 of each plate 10, 20 engage and "bite into" the spinous processes and lock implant 100 to the spinous processes.

Once plates 10, 20 are fixed to the adjacent spinous processes, rod 42 may then be removed from knob 41 so that there is nothing that extends proximally beyond plate 10. See FIG. 5. Rod 42 or a proximal portion of rod 42 can be removed from locking element 40 by any number of mechanisms. For example, the compressive force between plates 10, 20 that is necessary to ensure that plates 10, 20 can be compressed so that projections 15 "bite into" the spinous processes can be determined. Once this force is determined, the cross-sectional area of a segment of rod 42 can be locally decreased so that it fractures after the desired compressive force has been reached. This cross-sectional area can be computed based on the mechanical properties chosen for knob 41 and rod 42 of locking element 40. Alternatively, a mechanical connection, such as a thread located along the distal end of rod 42 and a tapped hole formed in knob 41, may be used. In such an embodiment, the user would be able to manually disengage rod 42 from knob 41 after plates 10, 20 have been fixed to the spinous processes. Also, a cutting device may be used to cut off a proximal portion of rod 42.

A method of implanting the spinal implant may include the following steps. After access to the desired spinal motion segment is obtained, proximal plate 10 is located adjacent to the proximal lateral sides of adjacent superior and inferior spinous processes. Where brace 30 is fixed to plate 20, proper placement of plate 10 ensures that brace 30 extends in the interspinous space through the sagittal plane. Where brace 30' is not fixed to plate 10', the distal end of brace 30' may be inserted through opening 11' in plate 10', after plate 10' is properly located adjacent the proximal lateral sides of the adjacent spinous processes, and moved distally through the interspinous space until flange 35 abuts the proximal medial face of plate 10' around opening 11'. With proximal plate 10 and brace 30 properly located with respect to the spinal segment, the distal end of brace 30 should extend past the distal lateral sides of the adjacent spinous processes. Distal plate 20 may then be placed over the distal end of brace 30 so that plate 20 is placed adjacent to the distal lateral sides of the adjacent superior and inferior spinous processes. Locking mechanism 40 may then be placed into lumen 31 through brace 30 such that the proximal end of rod 42 is first inserted into the distal end of brace 30 and moved proximally through brace 30 until knob 41 abuts the distal opening of brace 30. Rod 42 may continue to be pulled from the proximal side of brace 30 so knob 41 enlarges the distal portion of brace 30 and locks plate 20 onto brace 30 and with respect to plate 10. Continued proximal movement of locking mechanism 40 forces knob 41 further into the distal portion of brace 30, enlarging this portion of brace 30 and forcing distal plate 20 to move proximally into engagement with the distal lateral faces of the adjacent superior and inferior spinous processes. Once the surgeon is satisfied with the placement of implant 100, rod 42 may be cut or broken off of knob 41. For example, knob 41 may be connected to rod 42 by a frangible connection that may be broken by specific manipulation of rod 42. If desired, the distal portion of brace 30 extending beyond the distal face of distal plate 20 can be removed to minimize the space occupied by implant 100. However, it is contemplated that only a minor length of the distal portion of brace 30 will extend beyond the distal face of distal plate 20 after plates 10, 20 have been compressed into engagement with the spinous processes. Thus it may be unnecessary to remove any portion of the distal portion of brace 30.

Implant 100 may be formed of suitable biocompatible materials. For example, plates 10, 20 may be formed from stainless steel, titanium and its alloys, polymers such as PEEK, carbon fiber and the like. A softer, more ductile material, such as 316 stainless steel, may be used for brace 30. This material would allow brace 30 to deform without fracture and would not require an extremely high force to deform. A harder material, such as a cobalt chrome alloy, may be used for locking element 40. The various materials used for the parts of implant 100 may be considered in combination with the geometry of the various parts to obtain a customized force/implantation profile to facilitate implantation by the surgeon and achieve an optimized function.

While various embodiments of the spinous process fusion device are described herein, it should be understood that they have been presented by way of example only, and not limitation. Many modifications and variations will be apparent to the practitioner skilled in the art. The foregoing description of the spinous process fusion device is not intended to be exhaustive or to limit the scope of the invention. It is intended that the scope of the invention be defined by the following claims and their equivalents.

What is claimed is:

1. A spinal implant, comprising:
a first plate extending along a first longitudinal axis and having a first inner face configured to abut adjacent spinous processes and having projections extending from the first inner face;
a second plate extending along a second longitudinal axis and having a second inner face configured to abut the adjacent spinous processes and having projections extending from the second inner face;
a brace extending along a third longitudinal axis, the brace having a first diameter and including a flange fixed to a proximal end of the brace;
the first and second plates disposed along the brace such that the first and second longitudinal axes are transverse to the third longitudinal axis and the first inner face and the second inner face are oriented toward each other in spaced relation; and
a locking element engaging a distal end of the brace and longitudinally moveable relative to the brace such that longitudinal displacement of the locking element toward a proximal end of the brace modifies the brace such that a distal portion of the brace has a second diameter being greater than the first diameter and configured to prevent the second plate from being moved distally past a distal end of the brace, wherein longitudinal displacement of the locking element toward the proximal end of the brace narrows a distance between the first plate and the second plate.

2. The spinal implant of claim 1 wherein a proximal portion of the brace is fixed to the first plate.

3. The spinal implant of claim 1 wherein the locking element includes a distal end defined by a knob having a tapered proximal portion and a rod extending proximally from the knob.

4. The spinal implant of claim 3 wherein the knob has a circular cross section.

5. The spinal implant of claim 4 wherein the rod is connected to the knob by a frangible connection.

6. The spinal implant of claim 3 wherein the knob has a tapered proximal portion.

7. The spinal implant of claim 3 wherein the knob defines a third diameter that is greater than the second diameter and less than the first diameter.

8. The spinal implant of claim 1 wherein the flange prevents the first plate from being moved proximally past the proximal end of the brace.

9. The spinal implant of claim 1 wherein the brace defines a first configuration wherein the brace has a distal portion with an outer diameter having an initial diameter and a second configuration wherein the outer diameter of the distal portion of the brace has a subsequent diameter and wherein the subsequent diameter is greater than the initial diameter.

10. The spinal implant of claim 9 wherein the initial diameter is less than the first diameter and the subsequent diameter is greater than the first diameter.

11. A spinal implant, comprising:
a first plate extending along a first longitudinal axis and having a first inner face configured to abut adjacent spinous processes and having projections extending from the first inner face and having a first opening extending therethrough along a medial portion of the first plate;
a second plate extending along a second longitudinal axis and having a second inner face configured to abut the adjacent spinous processes and having projections extending from the second inner face and having a second opening extending therethrough along a medial portion of the second plate, the second opening defining a first diameter;
a brace extending along a third longitudinal axis and adapted to be disposed in the second opening and having a proximal portion connected to the first plate adjacent to the first opening, the brace being formed from a deformable material and defining a lumen having a second diameter, the brace including a flange fixed to the proximal portion of the brace and being configured to prevent the first plate from proximally moving off the brace; and
a locking element adapted to be moveably disposed at least partially in the brace, the locking element further comprising a distal knob and a proximal rod connected to the distal knob,
wherein the brace defines a first configuration wherein the brace has a distal portion with an outer diameter having an initial diameter and a second configuration wherein the outer diameter of the distal portion of the brace has a subsequent diameter and wherein the subsequent diameter is greater than the initial diameter.

12. The spinal implant of claim 11 wherein the distal knob has a tapered proximal portion.

13. The spinal implant of claim 12 wherein the distal knob defines a third diameter that is greater than the second diameter and less than the first diameter.

14. The spinal implant of claim 11 wherein the proximal rod defines a length that is adapted to be shortened.

15. The spinal implant of claim 11 wherein the initial diameter is less than the first diameter and the subsequent diameter is greater than the first diameter.

16. A method for implanting a spinal implant into an interspinous space defined by a superior spinous process and an inferior spinous process, comprising;
   placing a first plate, having a first opening, adjacent to proximal lateral sides of the adjacent spinous processes;
   placing a brace into the interspinous space, the brace including a flange fixed to a proximal portion of the brace preventing the first plate from proximally moving off the brace;
   placing a second plate, having a second opening, adjacent to distal lateral sides of the adjacent spinous processes such that the brace extends through the second opening;
   inserting a locking mechanism into a distal portion of the brace; and
   moving the locking mechanism proximally to change the distance between the first plate and the second plate and to lock the implant with respect to the superior spinous process and the inferior spinous process and to change the diameter of the brace along a distal portion of the brace from a first diameter to a second diameter, wherein the second diameter is larger than the first diameter.

17. The method of claim 16 further comprising changing the length of the locking mechanism from a first length to a second length wherein the second length is shorter than the first length.

18. The method of claim 16 further comprising placing the brace through the first opening.

\* \* \* \* \*